(12) United States Patent
Bulkes et al.

(10) Patent No.: US 6,445,953 B1
(45) Date of Patent: Sep. 3, 2002

(54) WIRELESS CARDIAC PACING SYSTEM WITH VASCULAR ELECTRODE-STENTS

(75) Inventors: Cherik Bulkes, Sussex; Arthur J. Beutler, Greendale; Stephen Denker, Mequon, all of WI (US)

(73) Assignee: Kenergy, Inc., Mequon, WI (US)

( * ) Notice: Subject to any disclaimer, the term of this patent is extended or adjusted under 35 U.S.C. 154(b) by 38 days.

(21) Appl. No.: 09/760,936

(22) Filed: Jan. 16, 2001

(51) Int. Cl.[7] ............................................. A61N 1/362
(52) U.S. Cl. ............................ 607/33; 607/37; 607/32; 607/126; 607/61
(58) Field of Search ........................... 607/2, 9, 10, 30, 607/32, 33, 37, 60, 61, 122, 126; 128/903; 623/1.15

(56) References Cited

U.S. PATENT DOCUMENTS

| | | | | |
|---|---|---|---|---|
| 4,524,774 A | * | 6/1985 | Hildebrandt | 128/903 |
| 5,170,802 A | * | 12/1992 | Mehra | 607/126 |
| 5,411,535 A | * | 5/1995 | Fuji et al. | 128/903 |
| 5,531,779 A | | 7/1996 | Dahl et al. | 607/119 |
| 5,649,952 A | | 7/1997 | Lam | 606/198 |
| 5,814,089 A | * | 9/1998 | Stokes et al. | 607/32 |
| 5,954,761 A | * | 9/1999 | Machek et al. | 600/375 |
| 6,061,596 A | * | 5/2000 | Richmond et al. | 607/40 |
| 6,141,588 A | * | 10/2000 | Cox et al. | 128/903 |
| 2001/0053926 A1 | * | 12/2001 | Whitehurst | 607/61 |
| 2002/0026228 A1 | * | 2/2002 | Schauerte | 607/122 |

* cited by examiner

Primary Examiner—Kennedy Schaetzle
(74) Attorney, Agent, or Firm—Quarles & Brady LLP

(57) ABSTRACT

A cardiac pacing apparatus has a source of pacing pulses that are transmitted through the animal by a radio frequency signal. An electrode-stent is implanted in a blood vessel adjacent to the point at which stimulation is desired. The electrode-stent contains an electrical circuit that is tuned to the radio frequency signal and which responds to receipt of that signal by applying an electric current to tissue of the animal.

10 Claims, 1 Drawing Sheet

WIRELESS CARDIAC PACING SYSTEM WITH VASCULAR ELECTRODE-STENTS

BACKGROUND OF THE INVENTION

The present invention relates to implantable medical devices which deliver energy to cardiac tissue for the purpose of maintaining a regular heart rate. Such devices are commonly referred to as cardiac pacing devices.

A remedy for people with slowed or disrupted natural heart beating is to implant a cardiac pacing device into the patient. A cardiac pacing device is a small electronic apparatus that stimulates the heart to beat at regular rates. It consists of a pulse generator, implanted in the patient's chest, which produces electrical pulses to stimulate heart contractions. Electrical leads extend from the pulse generator to electrode placed adjacent to specific muscles of the heart, which when electrically stimulated produce contraction of the adjacent heart chambers.

Modern cardiac pacing devices adapt their pulse rate to adjust the heartbeat to the patient's level of activity, thereby mimicking the heart's natural beating. The pulse generator modifies that rate by tracking the activity at the sinus node of the heart or by responding to other sensors that monitor body motion and rate of breathing.

Different pacing needs are met by adjusting the programming of the pulse generator and by the location of the electrodes. It is quite common that the leads extend through veins which enter the heart so that the electrodes can be placed in the muscle of the heart chamber requiring stimulation. This requires that the leads extend for some distance through the veins and may also necessitate that the leads pass through one or two heart valves. In other patients, patch electrodes are placed on the exterior heart surface with wires extending through tissue to the pacing device. With either type of lead placement, it is important that the electrodes be attached to the proper positions on the heart to stimulate the muscles and produce contractions. Thus it is desirable to properly locate the electrodes for maximum heart stimulation with minimal adverse impact to other physiological functions, such as blood circulation.

SUMMARY OF THE INVENTION

An apparatus, for electrically stimulating tissue of an animal, comprises a generator which produces a stimulation signal having pulses occurring at a rate corresponding to a rate at which stimulation is desired. Where the stimulation controls the animal's heart rate, the stimulation signal pulses occur at the heart rate that is desired for the animal. The stimulation signal is fed to a transmitter which emits a radio frequency signal.

An electrode-stent is implanted into a blood vessel of the animal at a location where the stimulation is desired, such as a blood vessel in a muscle of the heart. Upon receipt of the radio frequency signal the electrode-stent applies an electric current through tissue of the animal. In a preferred embodiment, the electrode-stent includes an antenna for receiving the radio frequency signal and a detector tuned to the frequency of the radio frequency signal. When the radio frequency signal is received, the detector produces an electric current that is applied to electrodes which in turn are in contact with the tissue to be stimulated.

The use of a radio frequency signal eliminates the need for hard wire connection between the source of the pacing signal and the stimulation electrodes. Therefore, a wire does not have to be permanently inserted through the vascular system of the animal.

DETAILED DESCRIPTION OF THE INVENTION

Figure 1:
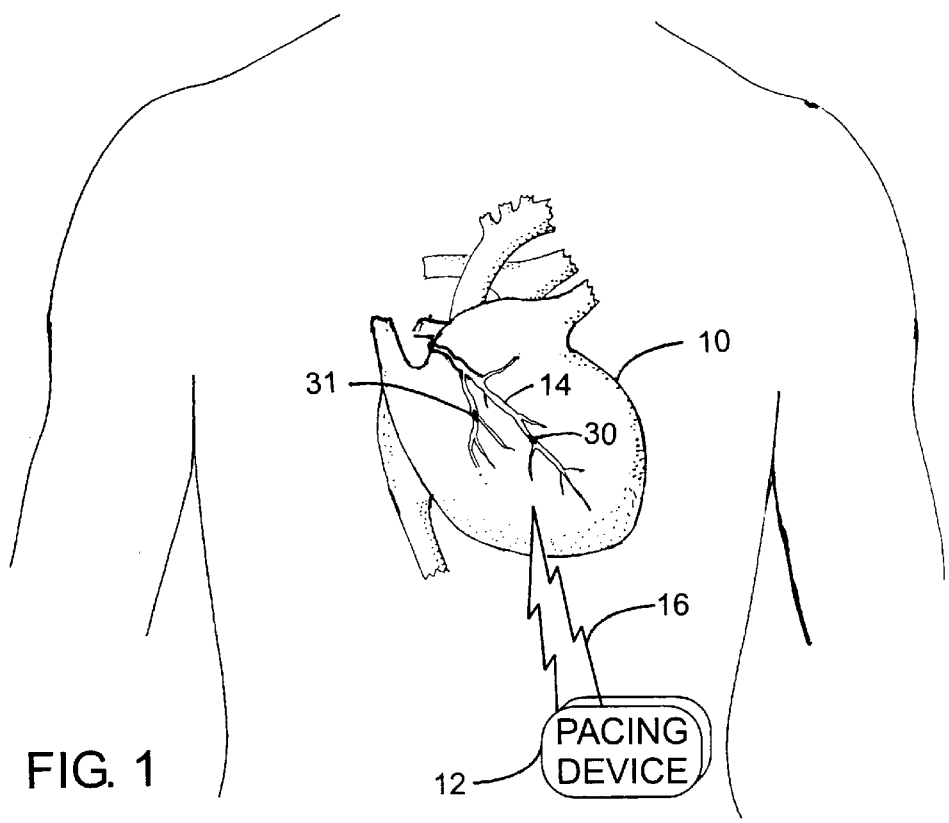
FIG. 1 is a diagrammatic view of the present invention implanted in a patient.

With initial reference to FIG. 1, an apparatus for applying electrical stimulation to pace a heart 10 comprises a pacing device 12 and one or more vascular electrode-stents located in veins 14 which supply blood to the heart muscles. As will be described in greater detail, the pacing device 12 emits a radio frequency signal 16 which produces an electric current in the implanted vascular electrode-stent thereby stimulating the heart muscle.

Figure 2:
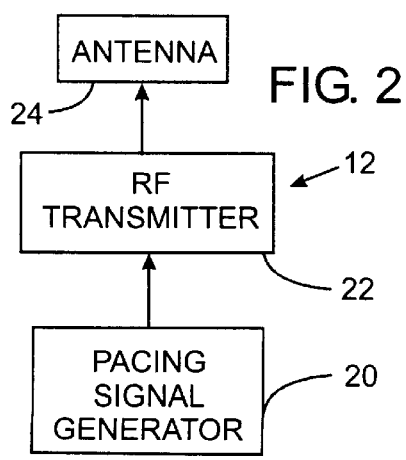
FIG. 2 is a schematic block diagram of the pacing device in FIG. 1.

Referring to FIG. 2, the pacing device 12 comprises a conventional pacing signal generator 20 similar to that utilized in previous cardiac pacers that use electrodes connected to leads. The internal circuitry and operation of the pacing signal generator is similar to those prior cardiac pacers. However, instead of the output stimulation signals being applied to the electrodes via leads, the pacing signals are applied to an input of a radio frequency (RF) transmitter 22. Both the pacing signal generator 20 and the RF transmitter 22 are powered by a battery (not shown). In response to the stimulation signal (also known as a pacing signal) from the generator 20, the radio frequency transmitter 22 generates a correspondingly long pulse of the radio frequency signal 16 that is transmitted throughout the chest cavity via an antenna 24. Preferably the antenna 24 either is located relatively close to the heart or is of a type which focuses the radio frequency signal toward the heart.

Figure 3:
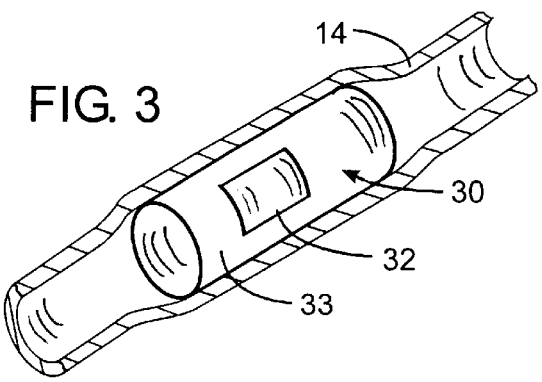
FIG. 3 is an isometric cut-away view of a cardiac vein with a vascular electrode-stent according to the present invention.

FIG. 3 illustrates an electrode-stent 30 that is placed in the vein 14 of the heart 10. The body 33 of the electrode-stent 30 has a design similar to well-known expandable vascular stents that are employed to enlarge a restricted vein or artery. Such vascular stents have a generally tubular design that initially is collapsed to a relatively small diameter enabling them to pass freely through an artery or vein of a patient.

The procedure for implanting the electrode-stent 30 is similar to that used for conventional vascular stents. For example, the balloon at the end of a standard catheter is inserted into the electrode-stent 30 in a collapsed, or reduced diameter, configuration. That assembly then is inserted through an incision in a vein or artery near the skin of a patient and threaded through the vascular system to the appropriate location adjacent the heart 10. Specifically, the electrode-stent 30 ultimately is positioned in a cardiac vein 14 adjacent to a section of the heart muscle where stimulation should be applied. The balloon of the catheter then is inflated to expand the vascular electrode-stent 30 which expansion also slightly enlarges the vein 14, as seen in FIG. 3 which embeds the electrode-stent 30 in the wall of the vein. This slight enlargement of the vein and the tubular design of the electrode-stent allows blood to flow relatively unimpeded through the device. The balloon is deflated, the catheter is removed from the patient, and the incision is closed. The electrode-stent 30 remains in the vein without any wire connecting an electrode to pacing device 12.

Figure 4:
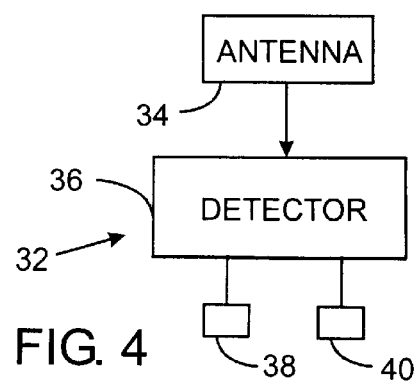
FIG. 4 is a schematic block diagram of an electrical circuit on the vascular electrode-stent.

With reference to FIGS. 3 and 4, the vascular electrode-stent 30 has a body 33 on which is mounted a signal receiving circuit 32. The signal receiving circuit 32 includes an antenna 34, a radio frequency signal detector 36, and a stimulator, that is formed by first and second electrodes 38 and 40, for example. The antenna 34 is connected to an input of the radio frequency signal detector 36. That detector is tuned to the frequency of the RF signal 16 that is emitted by the pacing device 12. Upon detecting the radio frequency signal 16, the detector 36 converts the energy of that signal into an electric current that is applied to the first and second electrodes 38 and 40. Those electrodes form an electric circuit path with the patient's heart tissue allowing for stimulation of that tissue. Thus, each time the pacing device 12 emits a radio frequency signal 16, a pulse of electrical current is produced in the vicinity of the electrode-stent 30, thereby stimulating the heart muscle adjacent to that electrode.

Therefore, instead of coupling the pacing device to the electrodes by wires extending through the vascular system and even the heart itself, the present invention employs radio frequency signals to provide that coupling. This eliminates the need for electrical leads that extend through the veins which can break thus disabling the cardiac pacing. Furthermore, the present electrode-stents 30 and 31 can be located in the cardiac veins 14 at points that are directly associated with the specific muscles requiring stimulation.

With reference to FIG. 1, a plurality of vascular electrode-stents 30 and 31 which are tuned to the same radio frequency can be positioned in cardiac veins at different locations in the heart to provide simultaneous stimulation of the adjacent tissue regions.

Alternatively, the plurality of electrode-stents 30 and 31, implanted in various veins of the heart muscle, can be tuned to different radio frequencies. In this embodiment, the radio frequency transmitter 22 also is tunable to produce output signals at several different radio frequencies, in response to an electrical control signal from the pacing signal generator 20. The pacing signal generator 20 now specifies the duration and the frequency of the RF signal 16 in order to select a specific electrode-stent to stimulate the heart muscle at a particular location. As a consequence, different portions of the heart muscle can be stimulated independently and sequentially by varying the radio frequency of the emitted signal 16 to correspond to the frequency to which the electrode-stent 30 in a given location is tuned. Furthermore, the plurality of electrode-stents 30 can be activated in a given sequence by producing a series of pacer signals at different radio frequencies. This enables the pacing device 12 to produce a sequential contraction of the heart chambers to increase cardiac efficiency.

The foregoing description was primarily directed to a preferred embodiment of the invention. Even though some attention was given to various alternatives within the scope of the invention, it is anticipated that one skilled in the art will likely realize additional alternatives that are now apparent from disclosure of embodiments of the invention. For example, although the invention has been described in the context of a cardiac pacing device, the inventive concept may be applied to devices for electrically stimulating other organs of the body, such as the brain for seizure control. Accordingly, the scope of the invention should be determined from the following claims and not limited by the above disclosure.

What is claimed is:

1. An apparatus, for electrically stimulating tissue of an animal, comprising:

a generator which produces a stimulation signal having pulses occurring at a rate corresponding to a rate at which stimulation is desired;

a transmitter connected to the generator and emitting a radio frequency signal in response to the stimulation signal; and a first electrode-stent for implantation into a blood vessel of the animal and which upon receipt of the radio frequency signal applies an electric current through tissue of the animal.

2. The apparatus as recited in claim 1 wherein the electrode-stent comprises:

an antenna for receiving the radio frequency signal;

a detector tuned to the frequency of the radio frequency signal and producing the electric current in response to receiving the radio frequency signal; and a plurality of electrodes for contacting the tissue of the animal and connected to the detector to receive the electric current.

3. The apparatus as recited in claim 2 wherein the electrode-stent has a body on which the antenna, the detector, and the plurality of electrodes are mounted.

4. The apparatus as recited in claim 1 wherein the electrode-stent has a shape which is expandable within the blood vessel from a first cross-sectional diameter to a second cross-sectional diameter.

5. The apparatus as recited in claim 1 further comprising a second electrode-stent for implantation into a blood vessel of the animal and which upon receipt of a radio frequency signal applies an electric current through tissue of the animal.

6. The apparatus as recited in claim 5 wherein the first electrode-stent and the second electrode-stent are tuned to a common radio frequency.

7. The apparatus as recited in claim 5 wherein the first electrode-stent and the second electrode-stent are tuned to different radio frequencies; and wherein the transmitter emits signals on the different radio frequencies.

8. A vascular electrode-stent for implanting into a blood vessel of an animal, the vascular electrode-stent comprising:

an antenna for receiving a radio frequency signal from a pacing device;

a detector tuned to the frequency of the radio frequency signal and producing an electric current in response to receiving the radio frequency signal; and a plurality of electrodes for contacting the tissue of the animal and connected to the detector to receive the electric current.

9. A method for artificially stimulating tissue of an animal, the method comprising:

inserting an electrode-stent into a blood vessel of the animal at a location at which electrical stimulation is desired;

producing a stimulation signal having pulses which occur at a rate corresponding to a desired frequency for the electrical stimulation;

converting the stimulation signal into a radio frequency signal which is transmitted through tissue of the animal; and the electrode-stent receiving the radio frequency signal and in response thereto applying an electric current through tissue of the animal.

10. The method as recited in claim 9 wherein the tissue comprises heart muscle and the rate of pulses of the stimulation signal corresponds to a rate at which the heart is desired to beat.

* * * * *